United States Patent [19]

Chamuel

[11] Patent Number: 4,706,021

[45] Date of Patent: Nov. 10, 1987

[54] CROSSED WIRE DEFECT DETECTOR EMPLOYING EDDY CURRENTS

[75] Inventor: Jacques R. Chamuel, Framingham, Mass.

[73] Assignee: The Charles Stark Draper Laboratory, Inc., Cambridge, Mass.

[21] Appl. No.: 583,490

[22] Filed: Feb. 29, 1984

Related U.S. Application Data

[63] Continuation-in-part of Ser. No. 521,311, Aug. 8, 1983, abandoned.

[51] Int. Cl.[4] .................. G01N 27/82; G01R 33/12
[52] U.S. Cl. ........................... 324/242; 324/240
[58] Field of Search .............. 324/234, 236, 239–243, 324/262, 263, 232, 227

[56] References Cited

U.S. PATENT DOCUMENTS

| | | | |
|---|---|---|---|
| 3,242,426 | 3/1966 | Burbank | 324/240 |
| 3,495,166 | 2/1970 | Lorenzi et al. | 324/228 |
| 3,609,531 | 9/1971 | Forster | 324/227 |
| 3,875,502 | 4/1975 | Neumaier | 324/241 |
| 4,331,919 | 5/1982 | Beckley | 324/240 |

Primary Examiner—Reinhard J. Eisenzopf
Assistant Examiner—Walter E. Snow
Attorney, Agent, or Firm—Weingarten, Schurgin Gagnebin & Hayes

[57] ABSTRACT

Apparatus for precise location of surface defects in a conductive material with a very high probability of detection of minute surface cracks. The invention comprises a first wire adapted to be disposed in parallel fixed spatial relation with the conductive surface and a second wire adapted to be disposed perpendicular to or angularly with respect to and intersecting the first wire and also in parallel fixed spatial relation with the conductive surface. The first wire is electrically energized to induce eddy currents in the conductive material opposite in direction and parallel to the first wire. The presence of a defect or flaw in the conductive surface induces transverse eddy currents which couple to the second wire. In the absence of a defect, there is minimal eddy current coupling to the second wire. The eddy current in the second wire is amplified or otherwise processed to provide an output signal indicative of the presence of a defect. The finite dimensions of the wires' point of intersection allows high resolution and minute defect detection. Alternatively, a multi-element eddy current array is fabricated consisting of orthogonally or angularly disposed wires replicated to form a wire matrix. First axis wires are selectively driven and second axis wires are selectively scanned to provide nondestructive inspection of a surface area of specified dimension and shape. In another embodiment of the invention, a first wire is adapted to be disposed in parallel fixed spatial relation with the conductive surface and second and third wires are angularly disposed with respect to the first wire. Means for differentially sensing eddy currents in the second and third wires are provided to produce an output indication representative of a defect. First, second and third wires may be replicated to form a three axis wire matrix with first axis wires selectively driven and second and third axis wires selectively scanned to provide nondestructive inspection of a specified surface area.

18 Claims, 9 Drawing Figures

CROSSED WIRE DEFECT DETECTOR EMPLOYING EDDY CURRENTS

This application is a continuation-in-part of application Ser. No. 521,311 filed Aug. 8, 1983, now abandoned.

FIELD OF THE INVENTION

This invention relates to sensors for detection of surface defects in conductive material and more specifically to a high resolution eddy current defect detector capable of rapid inspection of large surface areas.

BACKGROUND OF THE INVENTION

It is often of significant importance to be able to detect very small surface defects in critical componentry. Flaws of 0.010" or less may grow resulting in catastrophic or life threatening failures in aircraft components or other materials, objects or members when such members or components are subjected to high stress. Known ultrasonic and electromagnetic nondestructive test techniques have not proved effective in detecting defects of 0.010" in length reliably and repeatably.

Typical eddy current sensor employs an eddy current coil to sense the presence of surface flaws or defects. The resolution of such sensors depends upon the size of the coil, the electrical properties of the material under test, the frequency of the coil energizing signal in addition to other factors. These sensors depend upon a change in the impedance of a coil for defect detection. Detection capabilities of eddy current coil sensors are therefore limited due to the operational characteristic that coil sensors integrate over the coil area and reliable detection of flaws below 0.010" length by 0.005" depth has been problematic. (See K. J. Kryzwosz, R. E. Beissmer, and J. E. Doherty; 14th Symposium on NDE; San Antonio, Tex.; Apr. 19-21, 1983).

A recently disclosed eddy current sensor for surface defect detection utilizes a loop of wire as a driver and a receiver coil normal to the plane of the driver coil. The receiver coil is operative to detect tangential fields resulting from eddy current flow along edges of a defect. (See R. Langman, British Journal of NDT. pp. 8487, March 1979) The disclosed technique has several disadvantages; notably, the use of a circular coil receiver limits the resolution of the detector and a circular defect which is concentric with the coil may not be detected.

To scan a large area with a small coil eddy current probe necessitates time consuming mechanical scanning techniques which are costly to implement and which may fail to precisely locate small defects.

SUMMARY OF THE INVENTION

A defect detector that permits the detection and precise location of minute surface defects via induction of eddy currents in the surface of a conductive material and sensing of transverse eddy currents is disclosed. Surface defects below 10 mils in diameter are detectable in accordance with the present invention, and large surface areas may be rapidly inspected with a high probability of repeatable and reliable defect detection.

The detector comprises at least one first wire disposed proximate and parallel to the surface of a workpiece to be inspected. One end of the at least one first wire is electrically energized with the other ends of respective wires provided with a path for return current. Current flow through the at least one first wire induces eddy currents in the workpiece surface opposite in direction and parallel to the first wire. At least one second wire, employed as an electromagnetic receiver, is disposed perpendicular to or disposed angularly with respect to the first wire and so as to intersect the first wire. Second wires are also proximate and parallel to the workpiece surface under inspection. The at least one second wire is perpendicular to or angularly disposed with respect to the induced current. The presence of a surface defect in the vicinity of the intersection of the first and second wires causes eddy current flow around the defect edges thereby producing transverse eddy currents which couple to the second wire. In the absence of a defect at the intersection of the wire there is minimal eddy current coupling to the at least one second wire. Eddy currents coupled to the at least second wire are amplified or otherwise processed to provide an output signal indicative of the presence of a defect. The location of the intersection of the respective wires with respect to the workpiece surface may be varied manually or automatically to scan the entire workpiece surface.

In another embodiment of the invention a two-axis matrix of wires is employed to provide rapid large area inspection of a workpiece surface for defects. Each of the first axis wires are parallel and disposed in fixed spatial relation with respect to adjacent wires. Each of the second axis wires is also parallel to and in fixed spatial relation with adjacent second axis wires. The first axis wires are perpendicular to or angularly disposed with respect to each of the second axis wires and each first axis wire typically intersects at least one of the second axis wires. The wire matrix is disposed proximate and parallel to the workpiece surface under inspection. First axis wires are selectively energized and second axis wires are selectively sensed to scan the workpiece surface for defects at locations corresponding to the intersections of respective first and second axis wires.

In another embodiment of the invention, at least one first wire is disposed in parallel spaced relation with the conductive surface the work piece. At least one second axis wire and at least one third axis wire are disposed in parallel spaced relation with the conductive workpiece surface and the second and third axis wires are angularly disposed with respect to the at least one first axis wire. One end of each of the at least one first axis wire is selectively energized and opposing ends of the first axis wires are grounded to provide a path for return current. In a preferred embodiment second and third axis wires are angularly disposed at 45 degrees with respect to the first axis wires. Second and third axis wires are orthogonally disposed with respect to each other. Second and third axis wires are selectively and differentially scanned to provide an output indication representative of a defect proximate to the intersection of selected first, second, and third axis wires. Processing electronics of a type known in the art may be included to enhance defect recognition and/or otherwise cancel common mode noise.

A differential wire receiver may be used in any of the disclosed embodiments to minimize the sensitivity of the detector to lift-off and to reduce common mode noise.

DESCRIPTION OF THE DRAWINGS

The invention will be understood by reference to the following description in conjunction with the accompanying drawings in which.

DETAILED DESCRIPTION OF THE INVENTION

In accordance with the present invention a defect detector is disclosed that permits the detection of small defects in the surface of a conductive workpiece or a workpiece having a conductive surface.

Figure 1:
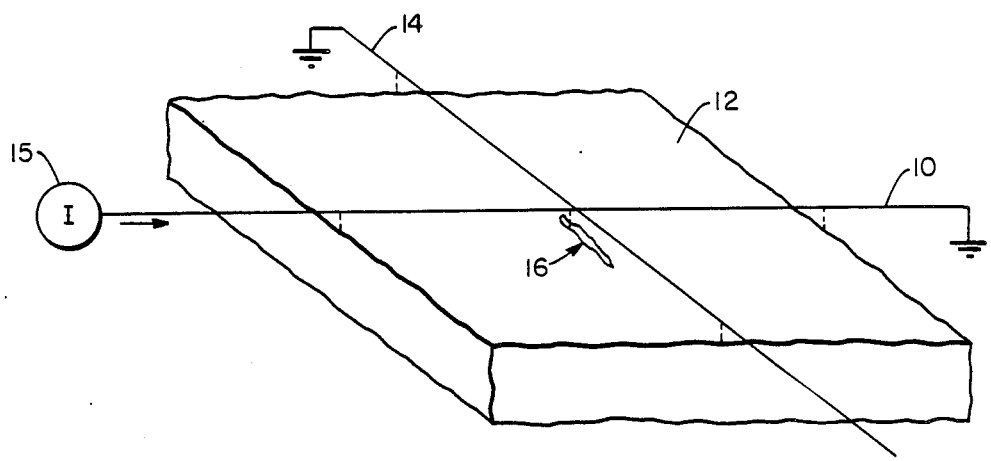
FIG. 1 is a pictorial representation of a two-wire eddy current defect detector in accordance with the present invention.

In one embodiment of the invention, the detector comprises a first wire 10 disposed in fixed spatial relation and parallel to a workpiece 12 surface to be inspected and a second wire 14 also disposed parallel to and in fixed spatial relation with the workpiece 12 surface, but orthogonally disposed with respect to the first wire 10. An AC or pulsed current is applied to one end of the first wire 10 by a source of current 15 and current flow through the wire 10 produces an eddy current in the workpiece surface opposite to the direction of current flow in the wire 10. The second wire 14 is employed as a receiver and senses eddy currents in the workpiece 12 surface substantially parallel to the second wire 14. The size of respective wires may vary depending upon the application, however, in one embodiment, #42 AWG wire was employed. In the absence of a defect, eddy currents flow along the surface of the workpiece 14 along a path perpendicular to the second wire 14 with minimal coupling to the wire 14 disposed perpendicular to the first wire 10. The presence of a defect 16 disturbs eddy current flow through the workpiece 12 and results in eddy current components transverse to the induced currents and parallel to the second wire 14. The transverse eddy currents are coupled to the second wire 14 employed as a receiver and are amplified or otherwise processed to provide an output signal indicative of defect presence. Each of the wires may be manually or automatically positioned with respect to the surface of the workpiece 12 or the workpiece may be moved with respect to the intersection of the wires to accomplish inspection of the entire surface of the workpiece 12. The respective wires 10 and 14 may be shaped to conform to a flat surface as illustrated in FIG. 1, a cylindrical surface, a spherical surface, or other desired surface configurations.

Figure 2:
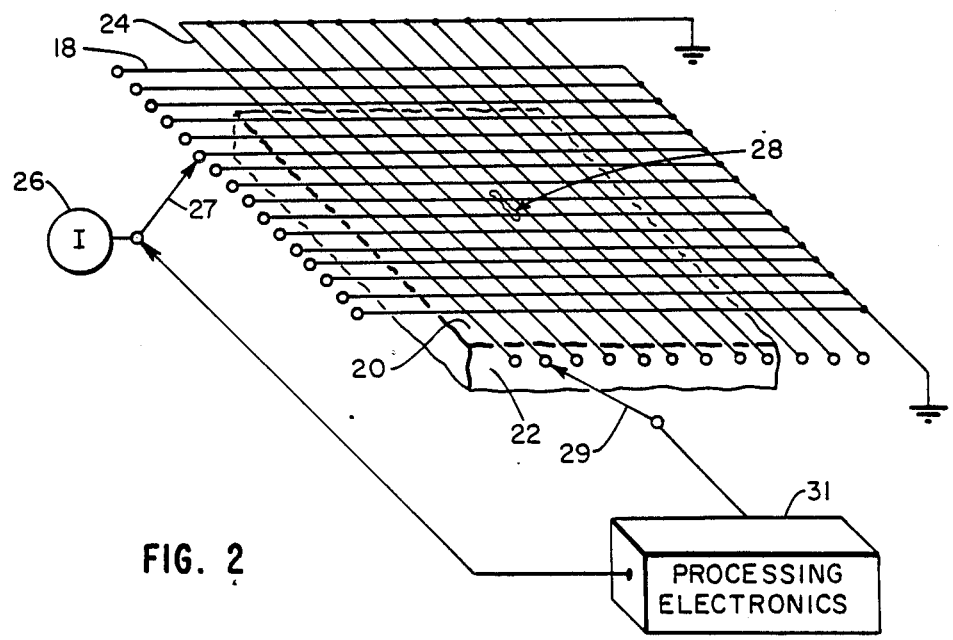
FIG. 2 is a pictorial representation of a wire matrix eddy current defect detector in accordance with the present invention.

Another embodiment of the invention applicable for rapid scanning of a workpiece surface for defects will be understood by reference to FIG. 2.

A plurality of parallel spaced first axis wires 18 are disposed proximate to the surface 20 of a workpiece 22. The wires 18 are in fixed spatial relation, one to the other, and are disposed in a plane parallel to the workpiece 22 surface 20 under inspection. A second plurality of wires 24 are disposed parallel to a second axis substantially perpendicular to the axis of the first wires 18. The wires 24 are also disposed in a plane substantially parallel to the surface 20 of the workpiece 22. Respective wires 18 and 24 may be overlaid or woven to form a wire matrix. A source 26, such as a continuous wave source or a pulse generator is used to selectively energize each of the first axis wires 18 through a switch 27, which may be electrical or mechanical. Energization of the first axis wires 18 induces eddy currents in the surface 20 of the workpiece 22 parallel to the selected wire 18. The presence of a defect 28 causes eddy currents transverse to the direction of eddy current induction and parallel to the second axis wires 24. The transverse eddy currents couple to the one of the second axis wires 24 at the wire intersection proximate to the defect. Eddy currents coupled to a selected second axis wire are sensed through scanning switch 29 and are amplified or otherwise processed in a unit 31 to produce an output signal indicative of the presence of the defect 28. The location of the defect 28 is indicated by unit 31 as the intersection of the energize first axis wire 18 and the selected second axis wire 24 that carries a signal. The location of the defect 28 corresponds to the intersection of those wires.

Figure 3A:
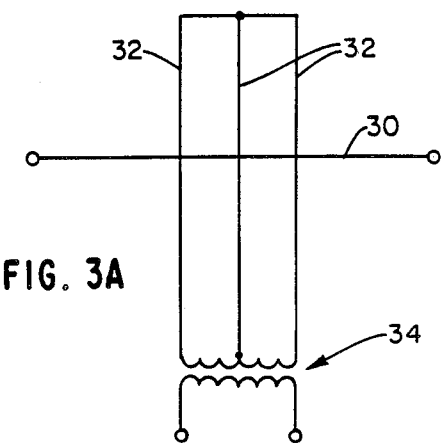
FIGS. 3A and 3B illustrate differential receivers operative in accordance with the present invention to reduce sensitivity to lift-off.
Figure 3B:
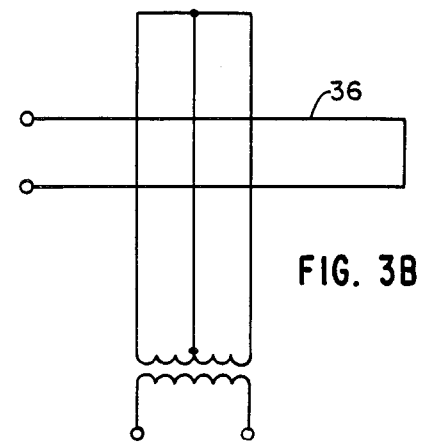

To provide improved insensitivity to induced noise and to minimize the effects of lift-off, the wires are configured as illustrated in FIGS. 3A and 3B to operate as differential receivers. A first axis wire 30 is energized. Three receiver wires 32 are disposed perpendicular to the energized wire 30 to detect transverse eddy currents and are connected to respective terminals of a center tapped transformer 34 primary coil. The presence of a defect near one of the wires 32 produces a current circulation through the transformer 34. The differential configuration of the wires 32 avoids common mode noise. The differential receivers may be coupled to an oscilloscope or other processing means via impedance matching within the transformer 34 or by use of any other suitable coupling means. As illustrated in FIG. 3B, a first axis wire 36 may also be provided in the form of a loop having two substantially parallel legs.

Figure 5A:
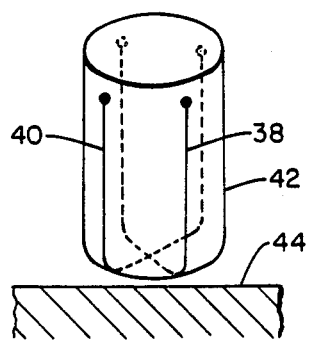
FIGS. 5A and 5B illustrate side and perspective views respectively of a probe operative in accordance with the present invention.
Figure 5B:
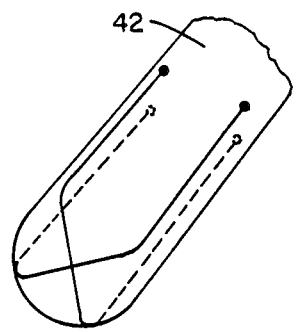

In the embodiment illustrated in FIGS. 5A and 5B, the detector is provided in the form of a probe to facilitate inspection of relatively small or inaccessible areas. First and second wires 38 and 40, respectively, as shown, are disposed along substantially orthogonal paths with the respective wires shaped to conform to a probe tip 42. One of the wires is energized and the other wire employed as a receiver of transverse current components in accordance with the prior disclosure. Additionally, as illustrated in FIG. 5A, wires 38 and 40 may be formed so as to lift away from surface 44 to be inspected to avoid sensing of eddy current components not associated with a defect due to fringe effects.

Figure 6:
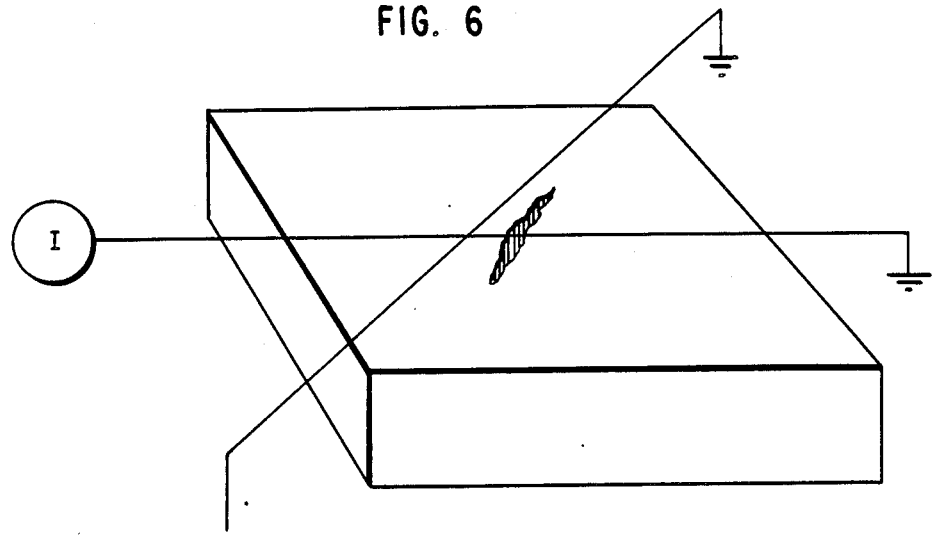
FIG. 6 is a pictorial representation of a two wire eddy current defect detector illustrating angularly disposed first and second wires.

In the embodiment of FIG. 6, a source of current 1 is employed to electrically energize a first wire 46 disposed is substantially parallel spaced relation from the surface 48 of a work piece 50 along the operative length of the wire. A second wire 52 is disposed in parallel spaced relation from the surface 48 of the work piece 50 along the operative length of the wire 52 and is disposed at a selected angle $\theta$ with respect to the first wire 46. The first wire 46 is electrically energized to induce an eddy current in the surface 48 of the work piece 50 opposite in direction to the current flow in the wire 46. The presence of a flaw or defect in the conductive surface produces transverse eddy currents in the workpiece surface around edges of the defect which couple to the at least one second wire 52. In the absence of defects, there is minimal eddy current coupling to the at least one second wire. The angle of the at least one second wire 52 with respect to the at least one first wire 46 may be varied by rotating the at least one second wire to optimize detection of defects having different major axes orientations.

First and second axis wires may be replicated in the form of a two axis wire matrix with first axis wires selectively energized and second axis wires selectively sensed to provide non-destructive inspection on a specified surface area.

Figure 7:
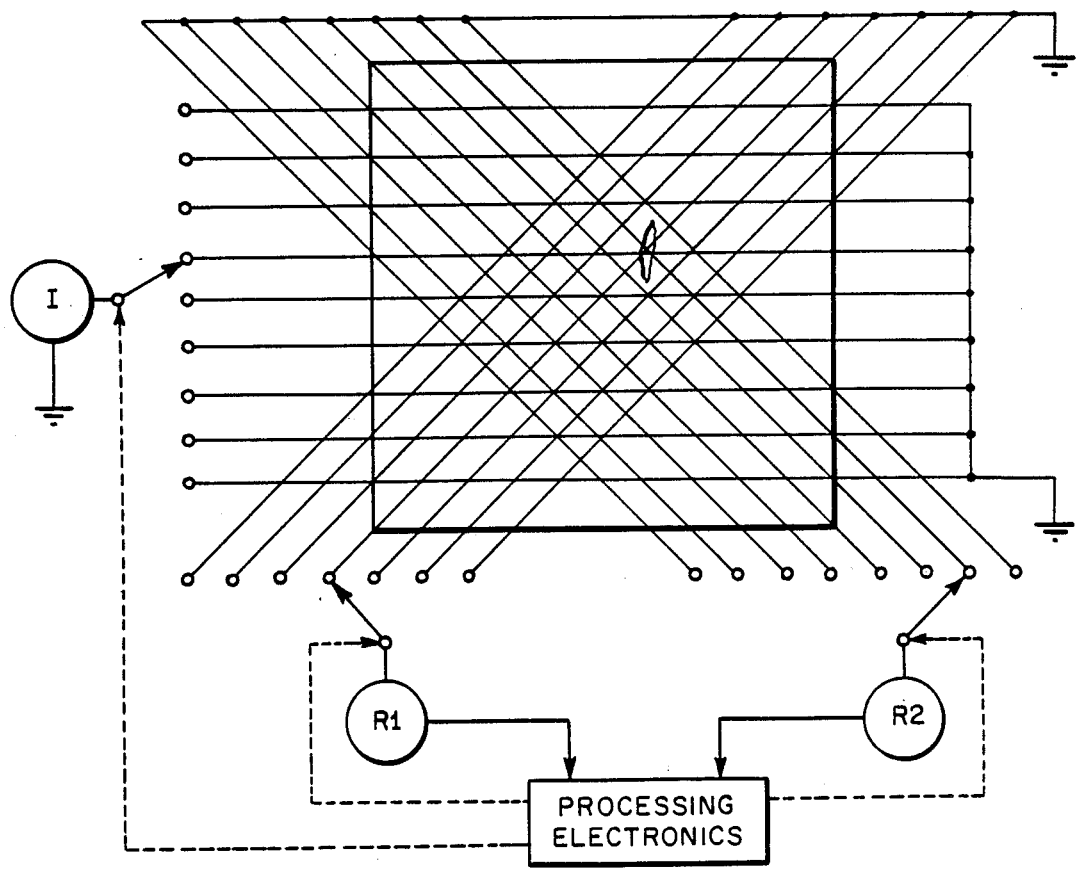
FIG. 7 is a pictorial representation of a wire matrix eddy current defect detector in accordance with the present invention illustrating wires angularly disposed and parallel to first, second and third axis.

In another embodiment of the invention shown in FIG. 7 at least one first axis wire 54 is disposed in parallel spaced relation with the surface 56 of a work piece 58. At least one second axis wire 60 and at least one third axis wire 62 are disposed in parallel spaced relation with the surface 56 of the work piece 58 and are angularly disposed with respect to the at least one first axis wire 54. One end of selected first axis wire 54 is selectively energized and opposing end of wires 54 are grounded to provide a path for return current. Second axis wires 60 and third axis wires 62 are selectively scanned and outputs from respective second and third axis wires are differentially sensed by processing electronics 64 to provide an output indication indicative of the presence of a defect proximate the intersection of respective first axis wires 54, second axis wires 60, and third axis wires 62. In a preferred embodiment of the invention illustrated in FIG. 7, second and third axis wires are orthogonally disposed with respect to each other and are disposed at 45 degree angles with respect to first axis wires 54. This embodiment permits nondestructive inspection of a surface area of specified dimension and shape. Processing electronics 64 may perform defect signal enhancement functions and to minimize undesirable common mode noise.

Figure 4:
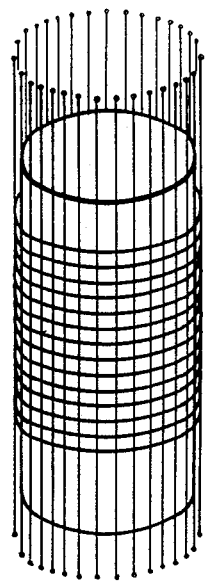
FIG. 4 is a detector in accordance with the present invention configured for inspection of a cylindrical surface.

A detector in accordance with the present invention is applicable for inspection of flat surfaces as illustrated in FIGS. 1 and 2, cylindrical surfaces as illustrated in FIG. 4, as well as other surface configurations.

The above described detector is illustrative of an apparatus permitting nondestructive inspection of a workpiece having a conductive surface by induction and detection of eddy currents in the workpiece surface. Other modifications, embodiments, and departures from the present disclosure are possible without departing from the inventive concepts contained herein. Consequently, the invention is to be viewed as embracing each and every novel feature and novel combination of features present in or possessed by the apparatus herein disclosed and is to be limited solely by the scope and spirit of the appended claims.

What is claimed is:

1. Apparatus for detection of defects in a workpiece having a surface of conductive material comprising:

at least one energization wire diposed parallel to a path along a first contour of said workpiece surface and having an operative length, each of said at least one energization wires adapted to be disposed adjacent to and substantially equidistant from said workpiece surface along said operative length;

at least one detection wire disposed parallel to a path along a second contour of said workpiece surface and having an operative length, each of said at least one detection wires adapted to be disposed adjacent to and substantially equidistant from said workpiece surface along said operative length, at least one of said detection wires intersecting at least one of said energization wires at a selected angle along the respective operative length thereof;

at least one of said at least one energization wire and said at least one detection wire comprising plural, spaced apart wires whereby a plurality of spaced apart intersections exist between detection and energization wires;

means operative to selectively induce a current in each of said energization wires to induce an eddy current along a path in the surface of the workpiece opposite in direction to the current in the respective energization wire;

the presence of a defect in the workpiece surface along the path of said eddy current producing a transverse eddy current which couples to an intersecting detection wire;

means operative to selectively sense, as a function of each of said plural intersections, the presence of a current in at least one of said detection wires and to produce a first signal representative of the selected detection wire current; and means operative to electronically process the first signal to produce an output signal representative of a surface defect proximate the intersection of the respectively selected energization and detection wires.

2. The apparatus of claim 1 wherein said apparatus includes plural detection wires and said selective sensing means includes means for differentially sensing selected ones of said detection wires.

3. The apparatus of claim 2 wherein said apparatus includes at least three detection wires and said selective sensing means includes an impedance matching transformer with two of said detection wires coupled to opposite primary ends of said impedance matching transformer and another one of said detection wires connected to a primary centertap of said transformer.

4. The apparatus of claim 1 wherein said energization and detective wires are shaped to conform to the shape of the workpiece surfaces.

5. The apparatus of claim 1 wherein said energization and detection wires are shaped to conform to a cylindrical surface.

6. The apparatus of claim 1 wherein each of said energization and detection wires is a #42 AWG wire or finer.

7. Apparatus for detection of defects in a workpiece having a surface of conductive material comprising:

a plurality of first spaced apart wires disposed parallel to a first path, each of said first path wires adapted to be disposed parallel and adjacent to the surface of said workpiece;

a plurality of second spaced apart wires disposed parallel to a second path, each of said second path wires adapted to be disposed parallel and adjacent said workpiece surface, each of said second wires substantially perpendicular to and intersecting each of said first path wires whereby a plurality of spaced apart intersections exist between said first and second wires;

means for selectively electrically energizing each of said first path wires to induce a current in the selected wire and to induce an eddy current along a path in the surface of the workpiece opposite in direction to the current in the selected wire;

the presence of a defect in the workpiece along the path of said eddy current producing a transverse eddy current which couples to a second path wire;

means operative to selectively sense, as a function of each of said plural intersections, the presence of a current in at least one of said second path wires and to produce an output signal representative of said transverse eddy current coupled to the respective second path wire in the presence of a defect; and the location of a defect being determinable as proximate to the intersection of the respective selectively energized first path wire and the selected second path wire.

8. The apparatus of claim 7 wherein said selective sensing means includes means for differentially sensing current along plural ones of said second path wires.

9. The apparatus of claim 8 wherein each of said selective sensing means includes an impedance matching transformer with two of said plural wires coupled to primary ends of an impedance matching transformer and one other of said plural wires connected to a primary centertop of said transformer.

10. The apparatus of claim 7 wherein said wires are shaped to conform to the shape of the workpiece surface.

11. The apparatus of claim 7 wherein said first and second path wires are shaped to conform to a cylindrical surface.

12. The apparatus of claim 7 wherein each of said first and second axis wires is a #42 AWG wire or finer.

13. A method for detection of defects in a workpiece having a surface of conductive material comprising the steps of:

providing a plurality of spaced apart intersections between first and second path wires comprising the steps of:

locating at least one wire having an operative length, parallel to a first path adjacent to and substantially equidistant from said workpiece surface along the operative length thereof;

locating at least one second wire having an operative length parallel to a second path adjacent to and substantially equidistant from said workpiece surface along the operative length thereof and substantially perpendicular to each of said at least one first path wires and adapted to be disposed adjacent to said workpiece surface, such that at least some of said second path wires intersect at least some of said first path wires to form said plurality of intersections;

electrically energizing selectively said first path wires to induce a current in the respective energized wire and to induce an eddy current along a path in the surface of the workpiece opposite in direction to the current in the energized wire;

coupling an eddy current transverse to the induced eddy current, and caused in the presence of a surface defect, to a second path wire; and selectively sensing, as a function of each of said plurality of intersections, said current coupled to the respective selected second path wire both in the presence and absence of a defect with a detector means and producing an output signal indicative of a defect; and coupling said detector means in turn to each of said second path wires and, upon production of said output signal indicative of a defect, producing a signal which identifies the location of said defect at the intersection of the respectively selected first path and second path wires.

14. A method for detection of defects in a workpiece having a surface of conductive material comprising the steps of:

locating a plurality of first wires parallel to a first path such that each of said first wires is disposed to conform to the surface of said workpiece;

locating a plurality of second wires parallel to a second path such that each of said second path wires is substantially perpendicular to and intersecting each of said first path wires whereby a plurality of spaced apart intersections exists between said first and second wires;

selectively electrically energizing each of said first path wires to induce a current in the selected wire and to induce an eddy current in the workpiece surface opposite in direction to the current in the selected wire, the presence of a defect in the surface of the workpiece along the path of the induced eddy current producing a transverse eddy current which couples to one of said intersecting second wires;

coupling a current detector in turn to each of said second path wires and producing an output signal representative of said coupled transverse eddy current; and determining the location of a defect as proximate to the intersection of the selectively energized first path wire with the respective second path wire as a function of said output signal.

15. A method of claim 14 wherein said coupling step includes the step of coupling said detector means including means for differentially sensing current along plural one of said second path wires in turn for indicating the present of current.

16. The apparatus of claim 1 further including:

means for supporting said at least one first and second path wires so as to permit placement of central portions of said wires adjacent to said workpiece with the ends of said wires located away from said workpiece.

17. Apparatus for detecting defects in a workpiece having a conductive surface comprising:

at least one first wire disposed along a first axis, each of said first wires having an operative portion disposed substantially equidistant from the surface of the workpiece;

at least one second wire disposed along a second axis, each of said second wires having an operative portion disposed substantially equidistant from the surface of the workpiece, disposed at a selected angle with respect to said first wires and intersecting at least one of said first wires;

at least one third wire disposed along a third axis, each of said third wires having an operative portion disposed substantially equidistant from the surface of the workpiece, and disposed at a selected angle with respect to said first axis wires and intersecting at least one first axis wire adjacent the intersection of one of said first wires with one of said second wires;

means operative to selectively induce a current in at least one first wire to induce an eddy current along a path in the surface of the workpiece opposite indirection to the current in said first wire;

the presence of a defect along the path of said eddy current producing a transverse eddy current which couples to an adjacent second axis wire and an adjacent third axis wire;

means operative to selectively sense the presence of a current in at least one of said second wires and to produce a first signed representative of said selected second wire current;

means operative to selectively sense the presence of a current in at least one of said third wires and to produce a second signal representative of said selected third wire current;

means operative to electronically process first signal from said second wire sensing means and the second signal from said third wire sensing means to produce an output signal representative of a surface defect proximate the intersection of selected first axis, second axis, and third axis wires.

18. The apparatus of claim 17 wherein each of said second axis wires is disposed at an angle of approximately 45 degrees with respect to the first axis wires, each of said third axis wires is disposed at an angle of approximately 45 degrees with respect to each of the first axis wires and said second and third axis wires are orthogonally disposed.

* * * * *